United States Patent
Buchanan

(10) Patent No.: US 7,604,479 B2
(45) Date of Patent: Oct. 20, 2009

(54) TIP WRENCH FOR ULTRASONIC DENTAL TOOL

(76) Inventor: L. Stephen Buchanan, 302 E. Cota St., 3rd Floor, Santa Barbara, CA (US) 93103

( * ) Notice: Subject to any disclaimer, the term of this patent is extended or adjusted under 35 U.S.C. 154(b) by 193 days.

(21) Appl. No.: 11/494,395

(22) Filed: Jul. 26, 2006

(65) Prior Publication Data
US 2008/0096163 A1    Apr. 24, 2008

(51) Int. Cl.
A61C 1/07    (2006.01)
(52) U.S. Cl. .......................... 433/119; 433/86; 433/143; 81/432
(58) Field of Classification Search .................. 433/119, 433/86, 143; 81/432, 487
See application file for complete search history.

(56) References Cited

U.S. PATENT DOCUMENTS

| | | | | |
|---|---|---|---|---|
| 2,193,615 A | * | 3/1940 | Ashley | 279/49 |
| 2,766,471 A | * | 10/1956 | McKenzie | 15/105 |
| 3,133,351 A | * | 5/1964 | Von Seggern | 433/119 |
| 3,368,280 A | * | 2/1968 | Friedman et al. | 433/86 |
| 3,589,012 A | | 6/1971 | Richman | |
| 3,654,502 A | * | 4/1972 | Carmona et al. | 433/119 |
| 4,019,254 A | | 4/1977 | Malmin | |
| 4,038,571 A | | 7/1977 | Hellenkamp | |
| 4,110,908 A | | 9/1978 | Cranston | |
| 4,682,949 A | | 7/1987 | Warrin | |
| 4,818,229 A | | 4/1989 | Vasile | |
| 5,094,617 A | | 3/1992 | Carr | |
| 5,133,661 A | | 7/1992 | Euvrard | |
| 5,261,922 A | | 11/1993 | Hood | |
| 5,318,570 A | | 6/1994 | Hood et al. | |
| 5,324,297 A | | 6/1994 | Hood et al. | |
| 5,359,996 A | | 11/1994 | Hood | |
| 5,733,119 A | | 3/1998 | Carr | |
| 5,776,155 A | | 7/1998 | Beaupre et al. | |
| 5,868,570 A | | 2/1999 | Hickok et al. | |
| 6,164,968 A | | 12/2000 | Feine | |
| 6,312,255 B1 | | 11/2001 | Hudak | |
| 6,722,882 B2 | | 4/2004 | Buchanan | |
| 6,811,399 B2 | | 11/2004 | Rahman et al. | |

(Continued)

FOREIGN PATENT DOCUMENTS

DE    1566241    3/1970

(Continued)

Primary Examiner—Cris L Rodriguez
Assistant Examiner—Hao D Mai
(74) Attorney, Agent, or Firm—Koppel, Patrick, Heybl & Dawson; Michael J. Ram

(57) ABSTRACT

A dental instrument comprising a handpiece with a threaded extension and a working tool for attachment to the extension includes a wrench mounted on the distal end of the handpiece for use in attaching the tool to the extension. The wrench comprises a nose piece mounted on the front end of the handpiece, said nose piece rotateable radially about the front end of the handpiece as well as longitudinally slidable forward of the distal end of the handpiece so that an opening in a front end of the nose piece extends over the hub of the tool. Rotating the extended nose piece radially around the front end of the handpiece causes the hub of the tool to rotate, attaching the tool to the threaded extension. The nose piece is then retracted to a storage position during use of the tool.

7 Claims, 5 Drawing Sheets

U.S. PATENT DOCUMENTS

| | | |
|---|---|---|
| 6,817,862 B2 | 11/2004 | Hickock |
| 6,948,935 B2 | 9/2005 | Nusstein |
| 2004/0126737 A1* | 7/2004 | Atkin et al. ................ 433/119 |
| 2004/0259054 A1* | 12/2004 | Mayer ....................... 433/119 |
| 2006/0068361 A1* | 3/2006 | Bergler et al. ................ 433/86 |

FOREIGN PATENT DOCUMENTS

| | | |
|---|---|---|
| WO | WO0074586 | 12/2000 |

* cited by examiner

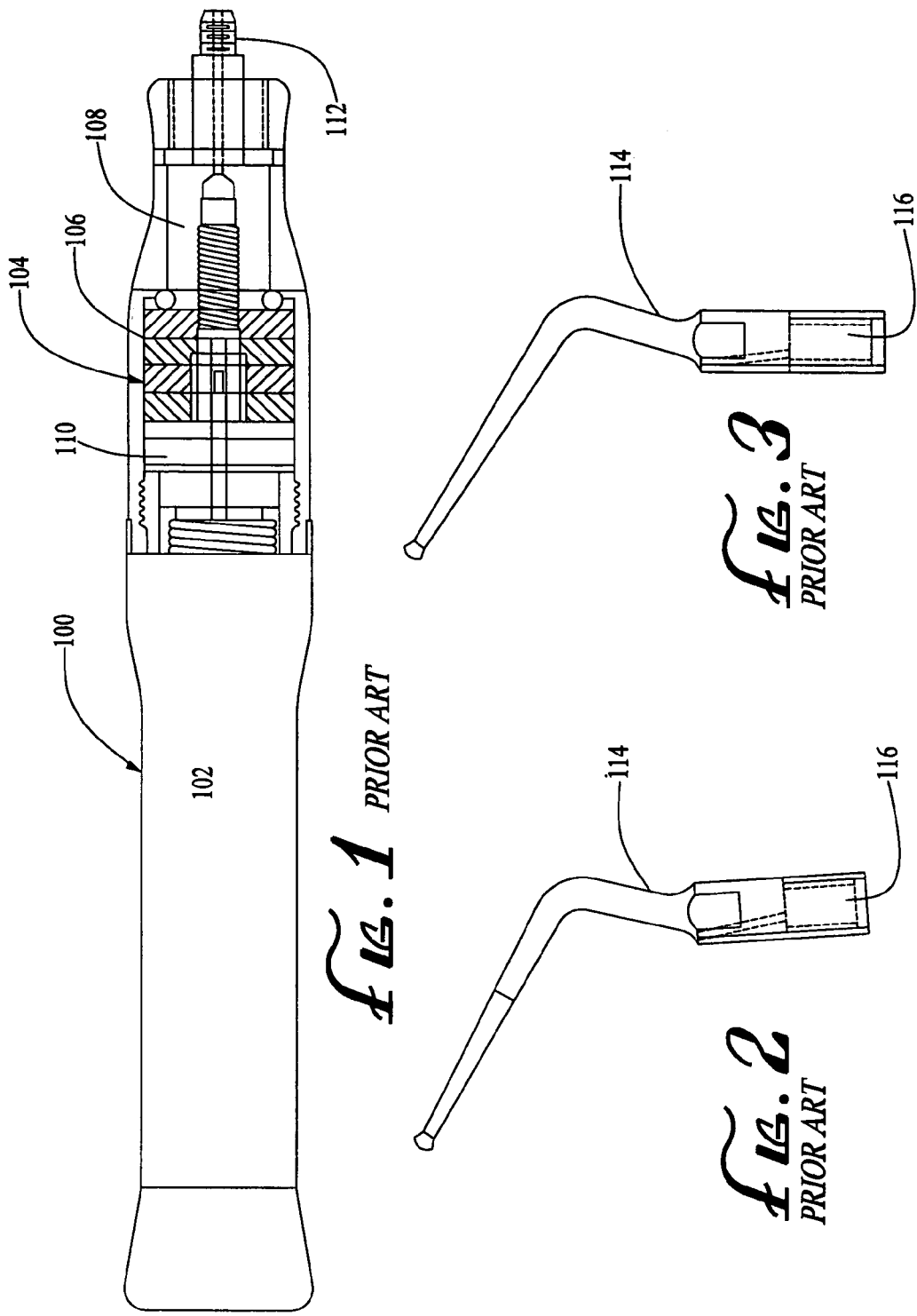

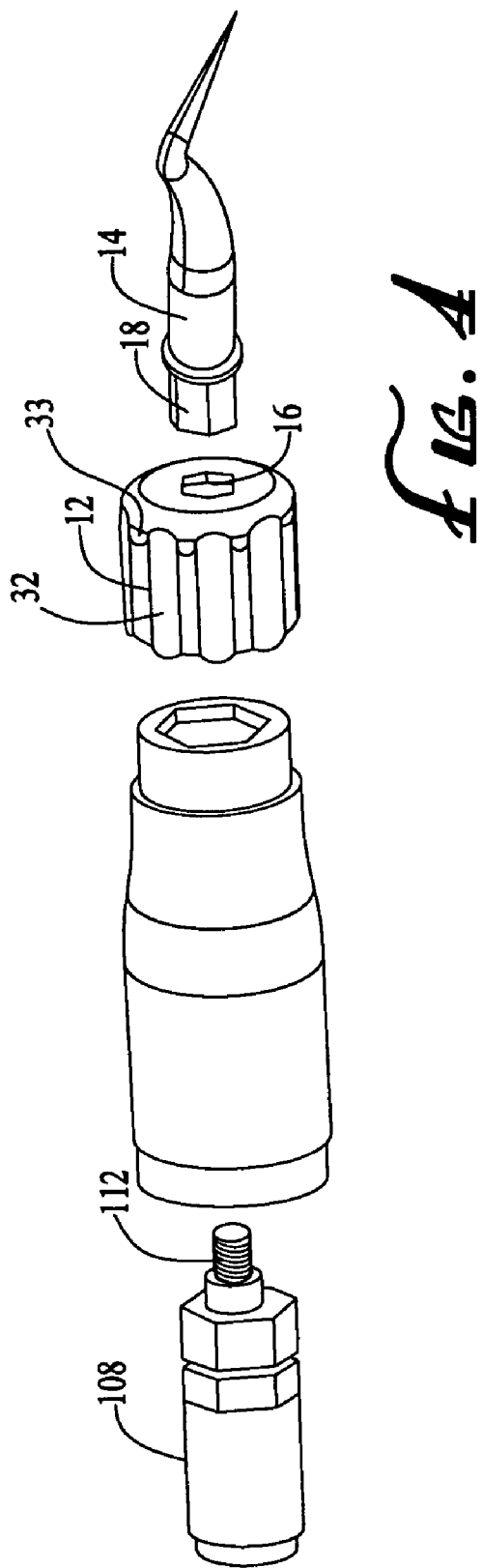
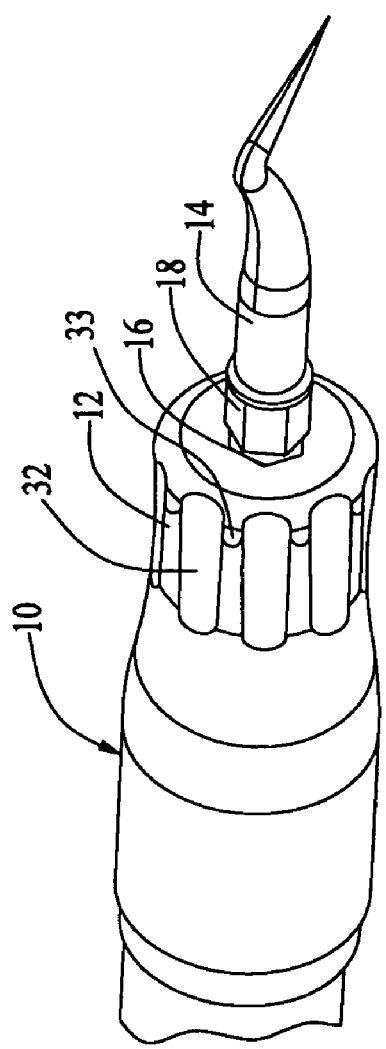

TIP WRENCH FOR ULTRASONIC DENTAL TOOL

BACKGROUND OF THE INVENTION

This invention relates to the attachment of a tool to a handpiece using a tightening tool moveably mounted on the operative end of the handpiece and more particularly to dental tools, particularly ultrasonic dental tools or instruments, and, more particularly, to a moveable structure on the forward end of an ultrasonic instrument handpiece for use in attaching an ultrasonic tip to the ultrasonic handpiece.

Ultrasonic devices and their tips are useful in carrying out a variety of dental procedures, such as tooth cleaning, preparation of cavities for filling and are particularly useful in preparing the canal of a tooth during root canal and endodontic procedures. Such ultrasonic dental tips are known, as shown in numerous patents of which U.S. Pat. Nos. 5,094,617, 5,133,661, 5,868,570, 6,722,882 and 6,811,399 and International Publication No. WO 00/74586 are examples. Most prior patents are directed to particular tip shapes to provide better visibility of the tooth and canal, improved maneuverability of the tip into the canal, operative end structure on the tip to provide smoother surfaces of the pulp chamber and prevent ditching, controlling depth of the tip so that the floor of the tooth canal is not penetrated, providing tips for removing, or not removing, different tissue (enamel, dentin, pulp stones) or tips of different materials, having different coatings or operating at specific frequencies for specific procedures such as cutting apically into calcified canals and for digging around posts that may have become embedded in the canal.

However, little attention has been provided to tools and procedures for easily and rapidly installing the tip on the handpiece or removing the tip for replacement with alternative functioning, or different size tips. The tips are typically threaded on to the handpiece requiring the dentist to use a separate wrench to grasp flat portions on the hub of the ultrasonic tip to remove the tip. U.S. Pat. Nos. 5,261,922, 5,318,570, 5,324,297 and 6,817,862 are representative of ultrasonic devices which have removable tips that have wrench flats formed on the hub of the tip for grasping with a separate wrench. Another mounting technique is shown in U.S. Pat. No. 5,776,155 which describes a prior art separate tightening tool applied to the tip hub and discloses a torquing device built into an adapter which remains over the tip hub and functions to retain the tip on the handpiece. U.S. Pat. No. 5,359,996 shows a tip with an end flange which is held against the transducer by a retaining nut slipped over the ultrasonic tip. This nut functions to hold the ultrasonic tip in place, does not function as a wrench and requires a separate wrench to apply and tighten the nut.

U.S. Pat. No. 4,038,571 to Hellenkamp shows an ultrasonic tool with a tip removeably threaded thereto. The tip base has exterior flats on its circumference. A rotatable cap on the front end of the tool has a hole in its front end to engage the flats on the tip when the tip base is inserted into the cap. When rotated, the cap functions to loosen or tighten the tip. During use as an ultrasonic cleaning tool the cap opening remains over the tip base which can result in biological materials becoming trapped within the cap.

My earlier issued patent U.S. Pat. No. 6,722,882, and FIGS. 1, 2 and 3 herein show an example of an ultrasonic dental handpiece and ultrasonic tips for placement thereon.

SUMMARY OF THE INVENTION

Ultrasonic tips with novel shape at their proximal ends and a tip tightening and loosening tool which interacts with that shape eliminates the need for a separate wrench to attach an ultrasonic tip to the handpiece is provided as a permanent component of the front end of the ultrasonic handpiece. The tool has a forward end with an opening therein sized to receive and act on a like-shaped structure integral with the proximal surface of the hub of the ultrasonic tip such that rotation of the tool around the longitudinal axis of the handpiece will cause the hub of the tip to be threaded onto or into the like-threaded forward end of the ultrasonic transducer. Once the tip is attached, the tool is retracted and it resides on the forward end of the handpiece out of contact with the ultrasonic tip. To use the tool it is moved axially over the attachment end of the tip and rotated in the proper direction to attach or remove the tip, as desired.

BRIEF DESCRIPTION OF THE DRAWINGS

FIG. 1 is a partial cross sectional side view of a prior art ultrasonic dental handpiece.

FIGS. 2 and 3 are side views of prior art ultrasonic tips having a hub for threadable connection to a transducer enclosed within the handpiece.

FIG. 4 is an expanded perspective side view of the ultrasonic tip, nose piece and front end of the handpiece.

FIG. 5 is a perspective side view of the ultrasonic tip secured to the handpiece with the nose piece retracted for use of the assembled device.

DESCRIPTION OF PREFERRED EMBODIMENTS

Figure 6:
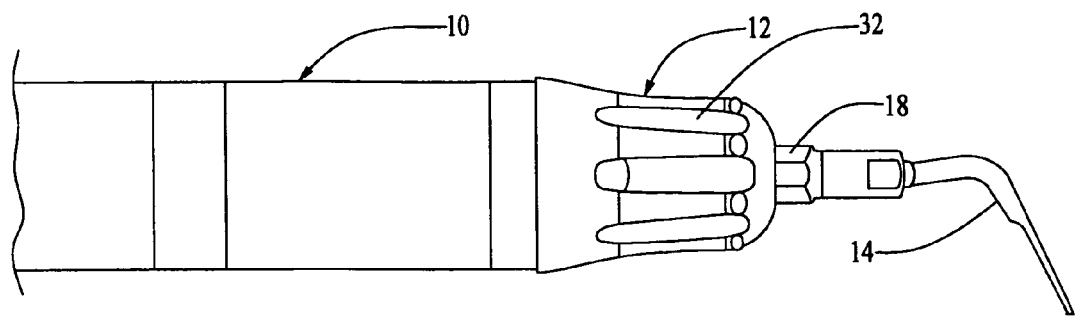
FIG. 6 is a side view of an ultrasonic handpiece incorporating features of the invention, with ultrasonic tip attached, the assembled device being shown in its operative mode.

FIG. 1 shows a typical prior art dental ultrasound handpiece 100. The handpiece 100 has a body 102 which is grasped by a clinician to perform a dental procedure. An ultrasonic transducer 104, typically comprising a stack of piezoelectric wafers 106 which vibrate upon being energized by oscillating electrical power supplied by a remotely located power supply (not shown) connected to the handpiece 100 by a cable (not shown). However, alternative power delivery means can be provided, such as a rechargeable or disposable battery pack. The piezoelectric wafers 106 are secured between a front retainer 108 and a back retainer 110. The front retainer 108, as shown in FIG. 1, has a threaded stud 112 extending longitudinally from the handpiece to receive an ultrasonic tip 114 which has a matching internally threaded socket (not shown). Alternative designs include a front retainer 108 with a threaded socket to receive an ultrasonic tip with an externally threaded stem. FIGS. 2 and 3 show typical prior art ultrasonic tips 114 which thread on to the threaded stud 112 shown in FIG. 1. Other alternative designs for connecting the ultrasonic tip to the handpiece are discussed above.

These tips are preferably constructed of a medical grade stainless steel, such as 13Cr-8Mo or 17-4PH stainless steel. However, they can alternatively be constructed of other medical grade materials such as titanium alloy, for example CP GR 4 or 5, or 6A14V. The working surface of the tip can also include a suitable micro-abrasive coating bound to the surface thereof, such as diamond particles, Zirconium oxide, or other common abrasive materials having a grit size generally ranging from about 160 and about 260. One skilled in the art will recognize that the grit size of the abrasive coating may vary widely, depending on the preference of the clinician and the procedure to be performed.

When power is supplied to the handpiece 100 the piezoelectric wafers 106 are caused to vibrate at ultrasonic frequencies which in turn causes the threaded stud to vibrate at ultrasonic frequencies, generally in the axial direction. This in turn imparts ultrasonic vibrations into the hub of the tip 14, 114 threaded on, or otherwise operatively coupled to, the handpiece. This causes the working end of the tip to resonate at its natural frequency generally in the plane of the tip. The amplitude of the vibration of the working tip will vary depending on the geometry of the tip and the power supplied by the handpiece 100.

Figure 7:
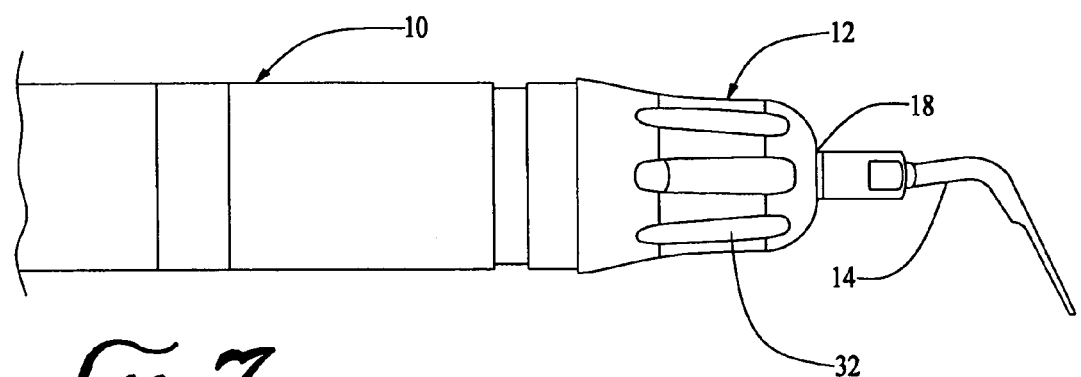
FIG. 7 is a side view of the ultrasonic handpiece and ultrasonic tip of FIG. 4 with the nose piece moved to a forward position for attachment or removal of the tip.
Figure 8:
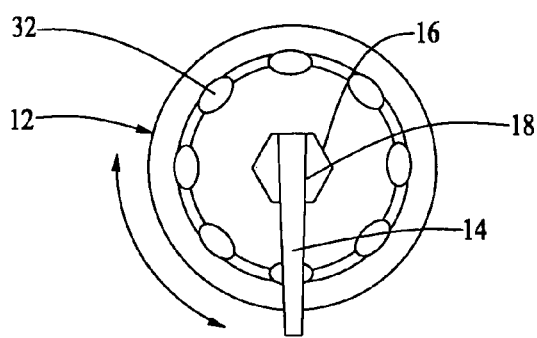
FIG. 8 is an end view of the ultrasonic tip, tip hub and attachment tool on the ultrasonic handpiece.
Figure 12:
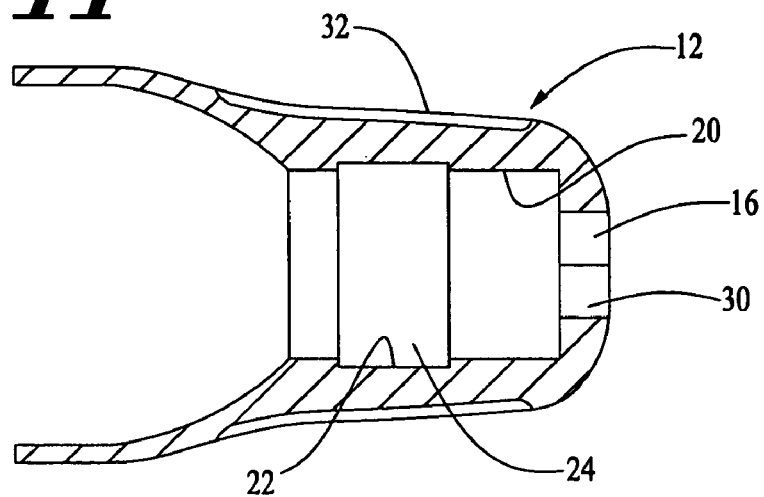
FIG. 12 is longitudinal cross sectional view of the nose piece of FIG. 9.
Figure 13:
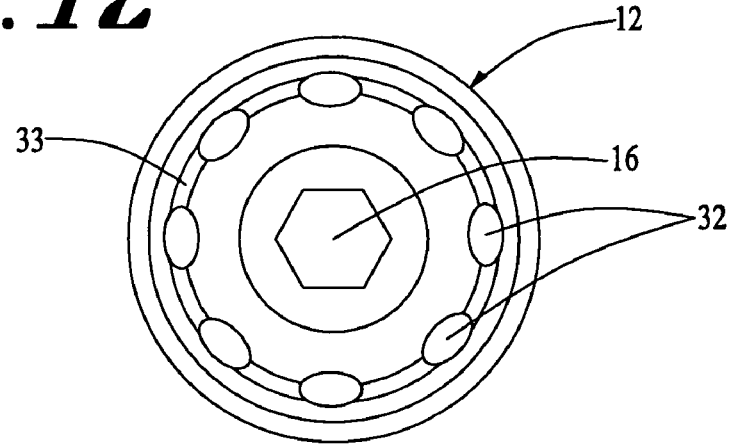
FIG. 13 is an enlarged front view of the nose piece of FIG. 9.

Referring to FIGS. 4-10, a device incorporating features of the present invention is shown. The handpiece 10 is constructed, and functions in the manner demonstrated by prior art devices of which FIG. 1 is an example. Added to this handpiece 10 is a moveable nosepiece 12 which is provided for use in easily attaching an ultrasonic tip 14 onto the threaded stud 112. As best shown in FIGS. 8, 12 and 13 the nose piece 12 has a central opening 16 in the forward end thereof. This central opening 16 has a periphery designed to interact with the hub 18 on the ultrasonic tip 14. The nose piece 12 functions as a wrench to grasp a similar shaped hub 18 on the ultrasonic tip 14. FIGS. 4 and 5 show an embodiment of a device incorporating features of the invention in an expanded and assembled view, respectively, with FIG. 5 showing the nose piece 12 in its retracted position and the dental handpiece with attached ultrasonic tip ready for use. In the embodiment shown in FIGS. 4, 5, 8, 12 and 13 the periphery of the opening 16 in the nose piece 12 is a six sided polygon designed to mate with a like sized hexagonal shape on the exterior hub 18 of the ultrasonic tip 14. However, one skilled in the art will recognize that various different peripheries can be used including, but not limited to, ovals, other polygons or a serrated or grooved circular openings.

In a preferred embodiment the tip 14 utilized with the present invention has a threaded recess within the hub 18 accessible through its proximal end to receive the external threads on stud 112 for securing the tip to the handpiece. This threaded connection which provides a connection between the stud 112 and the tip, instrument or tool 14 attached to the handpiece effectively transmits vibrations from the transducer to the tool 14. While the hub 18 is shown to threadably engage to the stud 112 it will be understood that the tip hub 18 can have external threads which thread into a threaded recess in the stud 112 or, within the broader aspects of this invention, any connection which efficiently transmits ultrasonic energy from the handpiece to the attached instrument. For example, in place of a threaded connection a variety of mechanical interlocking arrangements may be used such as are typically to chuck a tool to a drive mechanism.

Figure 9:
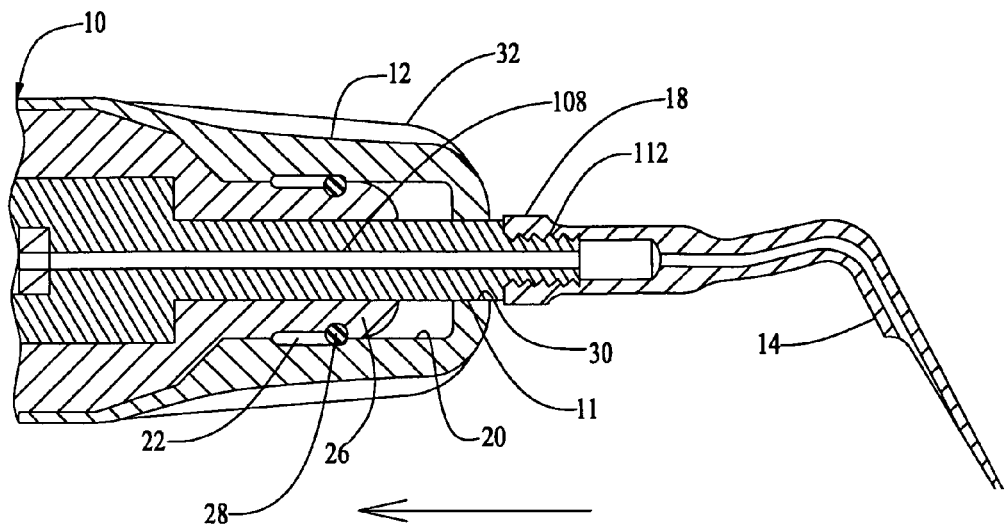
FIG. 9 is a longitudinal cut away view of the front portion of the ultrasonic handpiece with attached ultrasonic tip of FIG. 4 in its assembled configuration.
Figure 10:
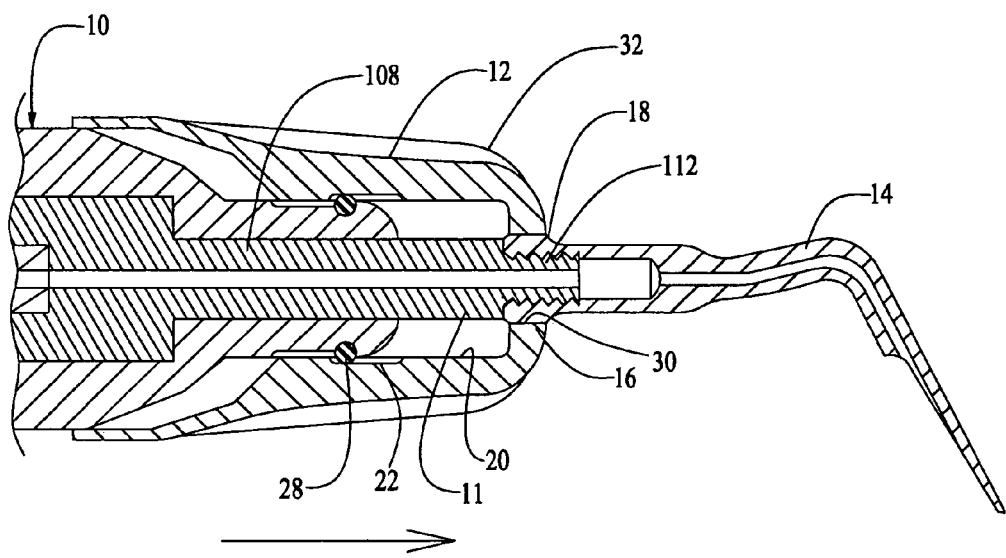
FIG. 10 is a longitudinal cut away view of the front portion of the ultrasonic handpiece and ultrasonic tip of FIG. 4 during the attachment of the tip to the threaded stud.
Figure 11:
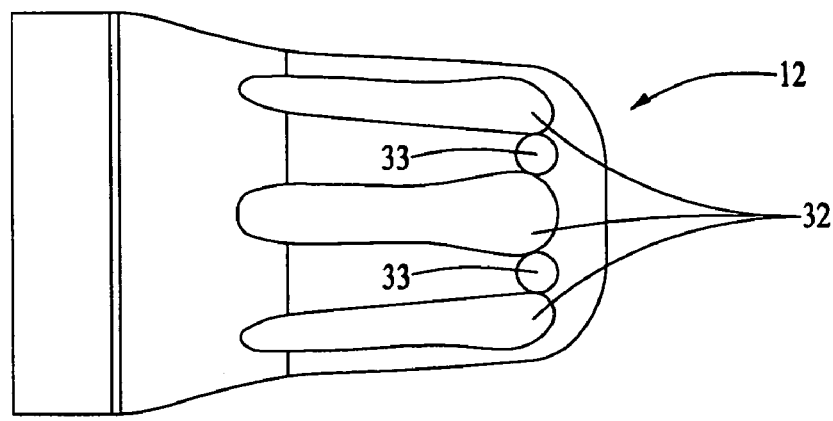
FIG. 11 is an enlarged side view of the nose piece which, when mounted on the handpiece, is used to place or remove the threaded tip on the ultrasound transducer.

FIG. 11 is a side view and FIG. 13 is a front end view of a preferred embodiment of the nosepiece 12. This nose piece is moveably mounted over the front end 11 of the handpiece 10. The nose piece 12 can be readily grasped between the fingers of the device user and easily rotated in the direction of the arrow shown in FIG. 8, around a central axis extending through the front end 11 of the handpiece 10 and the central opening 16. In addition, the nose piece 12 can be moved a fixed distance longitudinally from a rearward, rest position, as shown in FIGS. 4, 6 and 9, where there is no contact between the nose piece and the tip hub 18, to a forward, tip tightening position as shown in FIGS. 7 and 10, where the hub 18 on the tip 12 rests within the opening 16 in nose piece 12. As shown in the sectional view taken along the longitudinal axis of the nose piece, FIG. 12, the nose piece 12 comprises a hollow shell which has an inner longitudinal, cylindrical opening throughout its length with an internal diameter 20 which is slightly larger than the external diameter of the front end 11 of the handpiece 10 over which it extends. In the embodiment shown, a portion of the inner surface of the nose piece 12 also has a second, larger diameter 22 portion which provides a sliding zone 24. The front end 11 of the handpiece 10 has a radial circular groove 26 therein to receive a locking ring 28. The locking ring 28 has an outer diameter substantially the same as the second larger diameter 22 portion of the sliding zone 24. The locking ring 28 is preferably a flexible O-ring which also allows the nose piece to slide back and forth and to rotate thereover without obstruction or interfering friction. However, because the diameter of the sliding zone 24 is greater then the first diameter 20 and the locking ring protrudes into this sliding zone 24 the forward and rearward movement of the nose piece is restricted to the width of the sliding zone 24. In a preferred embodiment the width of the sliding zone 24 is from about 0.15 to 0.25 inches, preferably about 0.18±0.01 inches and the depth 30 of the opening 16, which is the portion of the nose piece that interacts with the hub 16 of the tip 14, is about 0.085 inches. However, greater movement longitudinally of the nosepiece, which is provided by widening the sliding zone, and a greater depth 30 of the opening 16 may be provided so that a longer length of the opening 16 in the nose piece can be provided to increase the area of contact with the outer surface of the hub 18.

To aid the operator in manipulating the nose piece 12, the outer surface thereof has longitudinally extending raised portions or bulges 32 spaced around its periphery to provide gripping features for rotating the nose piece 12 around the handpiece front end 11. However, numerous alternative structures including, but not limited to, grooves, dimples, a roughened surface, indentations, etc can be used to provide such a gripping surface. Also, raised radial structures 33 or indentations can be included to provide a gripping structure to aid in moving the nose piece longitudinally from its rest position to the forward, tip application position.

In a first procedure to use the nose piece 12 as a wrench for application of an ultrasonic tip 14 or other tool to the handpiece, the nosepiece 12 is advanced to its forward-most position. The hub 18 of a tip or tool is placed against the end of the threaded stud 112 and the tip is rotated, causing the threads on the stud 112 and in the hub 18 to mesh. This action causes the hub to become threaded onto the stub, as shown in FIG. 9. When the tip 14 is seated on the threaded stud 112 the noise piece is slid longitudinally forward in the direction of the arrow in FIG. 10 to its active position as shown in FIG. 10 and it is used as a tightening wrench to firmly engage the tip 14 to stud 112 after which the nose piece 12 is slid back longitudinally in the direction of the arrow in FIG. 9. To remove the tip 14 the above procedure is reversed.

While the above procedure includes manually returning the nosepiece 12 to its rest position it is also contemplated that a spring mechanism (not shown) can be included so that once the user of the device releases the noise piece it automatically returns to its rest position. This also would prevent the nosepiece 12 from inadvertently sliding forward over the hub during use of the tool in a dental procedure.

As various changes could be made in the above constructions and methods without departing from the scope of the invention, it is intended that all matter contained in the above description or shown in the accompanying drawings shall be interpreted as illustrative and not in a limiting sense. Also, the term "ultrasonic" generally refers to the use of piezoelectric transducers which vibrate at a frequency above the threshold of human hearing, typically above 20,000 Hz. However, those skilled in the art will recognize that vibrating handpieces suitable for dental or other medical procedures may use transducers other than piezoelectric transducers and these devices may vibrate at lower or higher frequencies and as the invention described herein may be utilized on devices that operate at lower frequencies are also meant to be included within the term "ultrasonic" even if such frequencies are substantially below 20,000 Hz. and substantially above 40,000 Hz., or frequencies therebetween. One such ultrasonic power supply and handpiece that has been successfully used with the instruments of the present invention is commercially available from Spartan Marketing Group, 1663 Fenton Business Park Court, Fenton, Mo. 63026. It is also contemplated that other electrical or mechanical means can be used to create vibration in the tip. It is further contemplated that the tip or tool attachment construction described herein may be used to easily attach a broad variety of operative tools to a handle and the invention described herein is not necessarily limited to the attachment of an ultrasonic tip to an ultrasound delivering handpiece or to the specific shapes or configurations of the interactive pieces.

I claim:

1. An improved ultrasonic dental instrument comprising a handpiece containing:
   a source of ultrasonic energy and a mounting stud extending from the source of ultrasonic energy through a front end of the handpiece and
   an ultrasonic tip removeably connected by an attachment hub thereon to said mounting stud and in operative communication with said source of ultrasonic energy,
   wherein said improvement comprises a wrench for use in attaching and removing the ultrasonic tip from the handpiece, said wrench comprising a nose piece mounted on the front end of the handpiece and slideable longitudinally from a retracted position to a forward position such that in the retracted position the nose piece does not extend over the attachment hub and is not in engagement with the attachment hub, said nose piece rotateable radially about the front end of the handpiece and when positioned longitudinally forward of the front end of the handpiece, an opening in a front end of the nose piece extends over the attachment hub of the ultrasonic tip, such that rotating the nose piece radially around the front end of the handpiece causes the attachment hub of the ultrasonic tip to rotate to effect securement of the ultrasonic tip to the mounting stud or removal of ultrasonic tip from the mounting stud.

2. The improved ultrasonic dental instrument of claim 1 wherein the front end of the handpiece includes a locking ring extending radially above the surface of the front end and the nose piece has an inner surface with a sliding zone of a defined length therein, said sliding zone positioned over the locking ring such that the nose piece can slide longitudinally forward a distance equal to the defined length of the sliding zone.

3. The improved ultrasonic dental instrument of claim 1 wherein the front end of the handpiece includes a locking ring extending radially above the surface of the front end and the nose piece has an inner surface with a sliding zone of a defined length with a forward edge and a rear edge such that when the locking ring rests against the rear edge of the sliding zone the opening in the front end of the nose piece extends over the attachment hub of the ultrasonic tip and when the locking ring rests against the front edge of the sliding zone the opening in a front end of the nose piece does not extend over the attachment hub of the ultrasonic tip.

4. The improved ultrasonic dental instrument of claim 1 wherein the opening in the front end of the nose piece has a polygonal shaped periphery and the hub of the ultrasonic tip has the same or a complementary shape and the inner dimensions of the opening is substantially the same as the outer dimensions of the hub to provide an interlocking fit between the opening and the hub.

5. In an instrument comprising at least a handpiece with a forward end and a tip having a hub removeably attached to an extension from the forward end of said handpiece, the hub having a defined outer geometric cross section, a rotateable and longitudinally extendable nose piece on the forward end of the handpiece, the nose piece having a opening in a forward end thereof, said opening having the same defined geometric shape on the walls of said opening and cross sectional dimensions substantially the same as the hub, the nose piece moveable from a rest position not extending over the hub to an attachment position extending over and in contact with the outer geometric cross section of the hub such that, in the attachment position, rotation of the nose piece causes the tip hub to rotate a like distance to cause the hub to become attached to or detached from the extension from the forward end of said handpiece.

6. A tool assembly comprising a handpiece and a tool tip for attachment to a threaded extension on a distal end of the handpiece,
   the tool tip having a distal working end and a proximal hub with an internally threaded lumen therein for receiving and mating with the threaded extension,
   the handpiece having a wrench mounted on the distal end thereof, said wrench rotateable about a central axis of the hand piece and reversibly slideable longitudinally from a rest position wherein the wrench does not extend over the proximal hub to an attachment position distal to the rest position wherein the wrench extends over the proximal hub and at least partially surrounds the threaded extension,
   the proximal hub having an outer surface adapted to receive and interact with the wrench such that when the tool tip hub is positioned on the threaded extension and the wrench is in its attachment position, rotation of the wrench around the central axis causes the hub to rotate onto or off of the threaded extension and when and the wrench is in its rest position, rotation of the wrench around the central axis does not contact the hub and does not cause the hub to rotate onto or off of the threaded extension.

7. The tool assembly of claim 6 wherein the outer surface of the proximal hub has a non-circular periphery or a circular periphery with a serrated or roughened surface and the wrench has a central opening with a complementary periphery.

* * * * *